United States Patent [19]

Russell et al.

[11] Patent Number: 4,823,807
[45] Date of Patent: Apr. 25, 1989

[54] DEVICE FOR NON-INVASIVE DIAGNOSIS AND MONITORING OF ARTICULAR AND PERIARTICULAR PATHOLOGY

[75] Inventors: I. Jon Russell; Thomas C. Carlson; Gilbert A. Vipraio, all of San Antonio, Tex.

[73] Assignee: Board of Regents, Univ. of Texas System, Austin, Tex.

[21] Appl. No.: 155,033

[22] Filed: Feb. 11, 1988

[51] Int. Cl.$^4$ ........................... A61B 5/10; A61B 5/12
[52] U.S. Cl. ..................................... 128/773; 128/774; 128/782
[58] Field of Search ........................ 128/773, 774, 782

[56] References Cited

U.S. PATENT DOCUMENTS

| 3,181,528 | 5/1965 | Brackin | 128/773 |
| 4,436,099 | 3/1984 | Rafteponlos | 128/774 |
| 4,437,473 | 3/1984 | Mollan | 128/773 |

FOREIGN PATENT DOCUMENTS 8504564 10/1985 PCT Int'l Appl. .................. 128/773

OTHER PUBLICATIONS

Thompson et al, Engineering in Medicine, vol. 7, No. 2, Apr. 1978, pp. 84–92.
Chu et al., "Detection of Knee Joint Diseases Using Acoustical Pattern Recognition Technique," J. Biomechanics, vol. 9, pp. 111–114, 1976.
Russell, "Clinical Utility of Acoustic Arthrography and Tendonography," Abstract, American Rheumatism Association, Annual Scientific Meeting, Anaheim, Jun. 4–8, 1985.
"Noninvasive Test Can Distinguish Arthritic Joint by Noisy Movements," Internal Medicine News, vol. 19, No. 11, p. 55, 1986 (citing Bol. Assoc. Med. P.R., 78:9–11, 1986).
Rolin et al., "The Correlation of Temporomandibular Joint Sounds With Joint Morphology in Fifty-five Autopsy Specimens," J. Oral Maxillofac. Surg., 43:194–200, 1985.
Eriksson et al., "Temporomandibular Joint Sounds in Patients With Disc Displacement," Int. J. Oral Surg., 14:428–436, 1985.
OMEGA Temperature Measurement Handbook and Encyclopedia, Omega Engineering Inc., One Omega Drive, Box 4047, Stamford, CT, 06907, pp. R–33 to R–51, 1985.
"Detecting Arthritis," U.S. News and World Report, pp. 55, Aug. 18, 1986.
"Microphone May Aid Arthritis Diagnosis," Medical World News, p. 75, Nov. 10, 1986.
"Never Mind How Your Joints Feel, What Do They Sound Like?", Business Week, p. 77, Feb. 2, 1987.
"A New Non-Invasive Method for the Diagnosis of Large-Joint Arthritis: Rectifying-Demodulating Phonopneumography", Boletin–Association Medica De Puerto Rico, vol. 78, pp. 9–11, 1986.

Primary Examiner—Francis Jaworski
Assistant Examiner—John C. Hanley
Attorney, Agent, or Firm—Arnold, White & Durkee

[57] ABSTRACT

Arthritis and related diseases are diagnosed by recording sound from a joint moving against a predefined resistance or a controlled velocity, and correlating the acoustic amplitude and instantaneous frequency with the joint angle. A preferred apparatus includes an articulated restraint for receiving a limb, a hydraulic pump and flow control valve for resisting joint movement, a pressure gage for measuring the torque about the joint, a position sensor sensing the joint angle, a noise cancelling microphone or an accelerometer for sensing sound from the joint, an amplifier and filter for amplifying and filtering the acoustic signal from the microphone or accelerometer, a frequency-to-voltage converter and an amplitude detector for determining the instantaneous frequency and amplitude of the filtered acoustic signal, an analog-to-digital converter for obtaining simultaneous numerical samples of the instantaneous frequency, amplitude, and torque, and a microcomputer programmed to display and record the instantaneous frequency and amplitude as a function of the joint angle, measured by either a digital shaft encoder or a potentiometer.

20 Claims, 12 Drawing Sheets

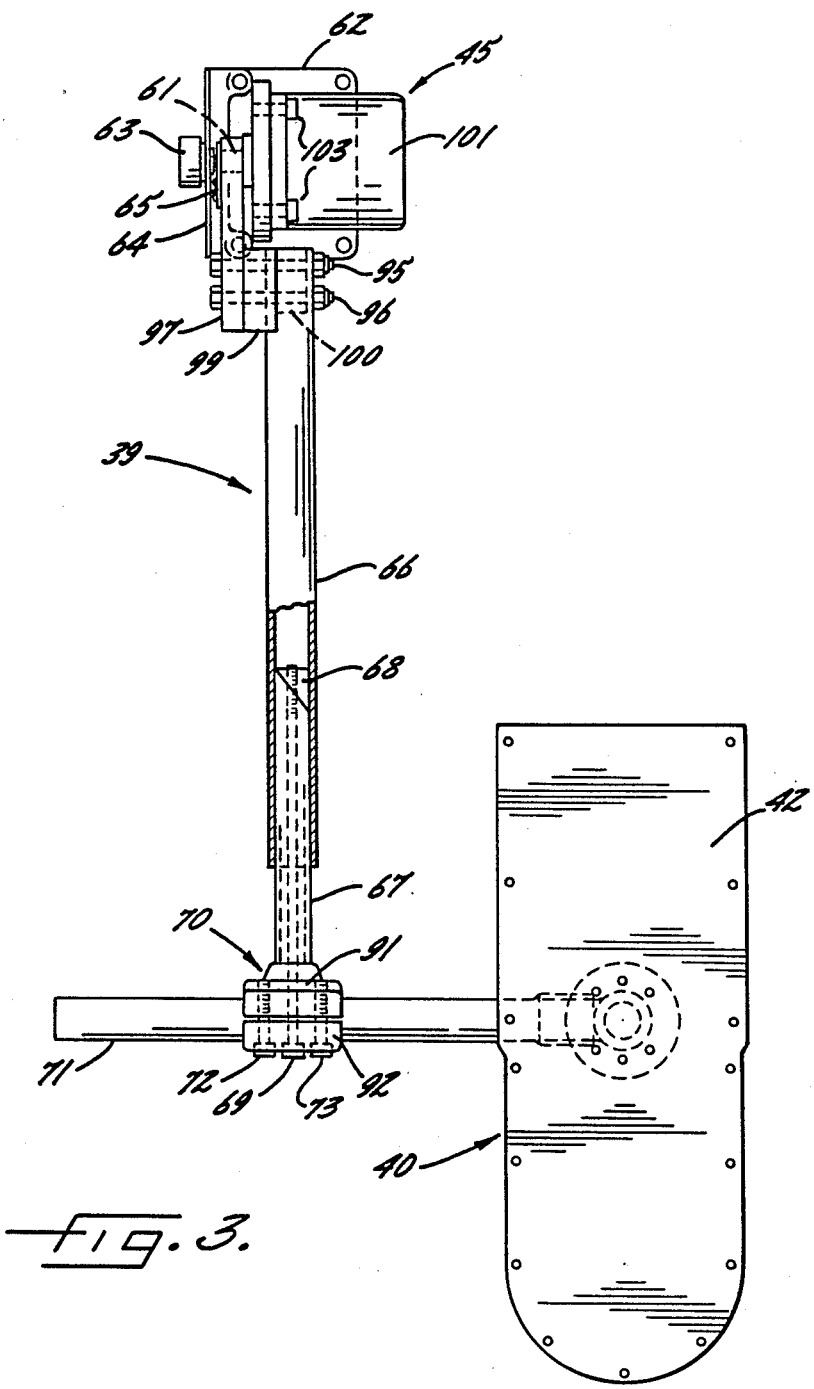

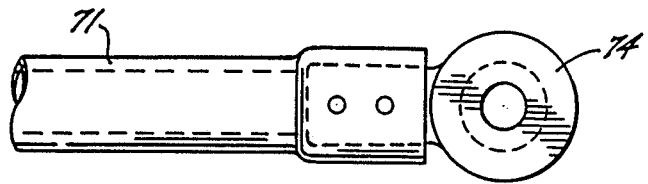
fig. 8.
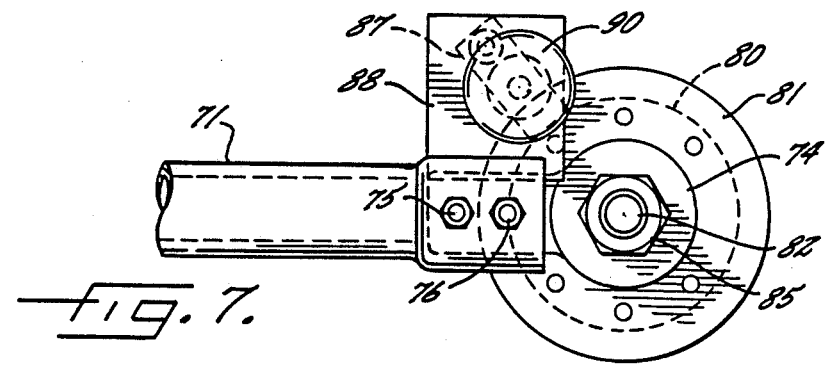
fig. 7.
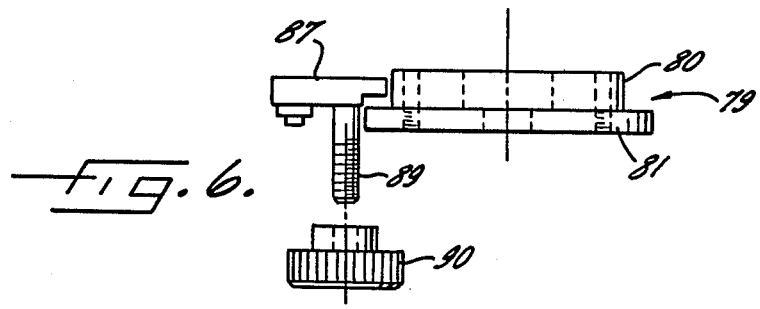
fig. 6.
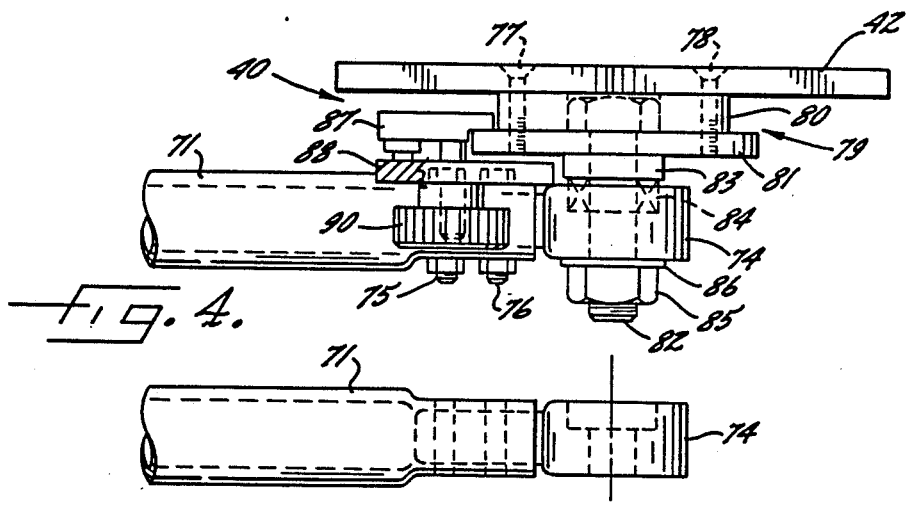
fig. 4.
fig. 5.

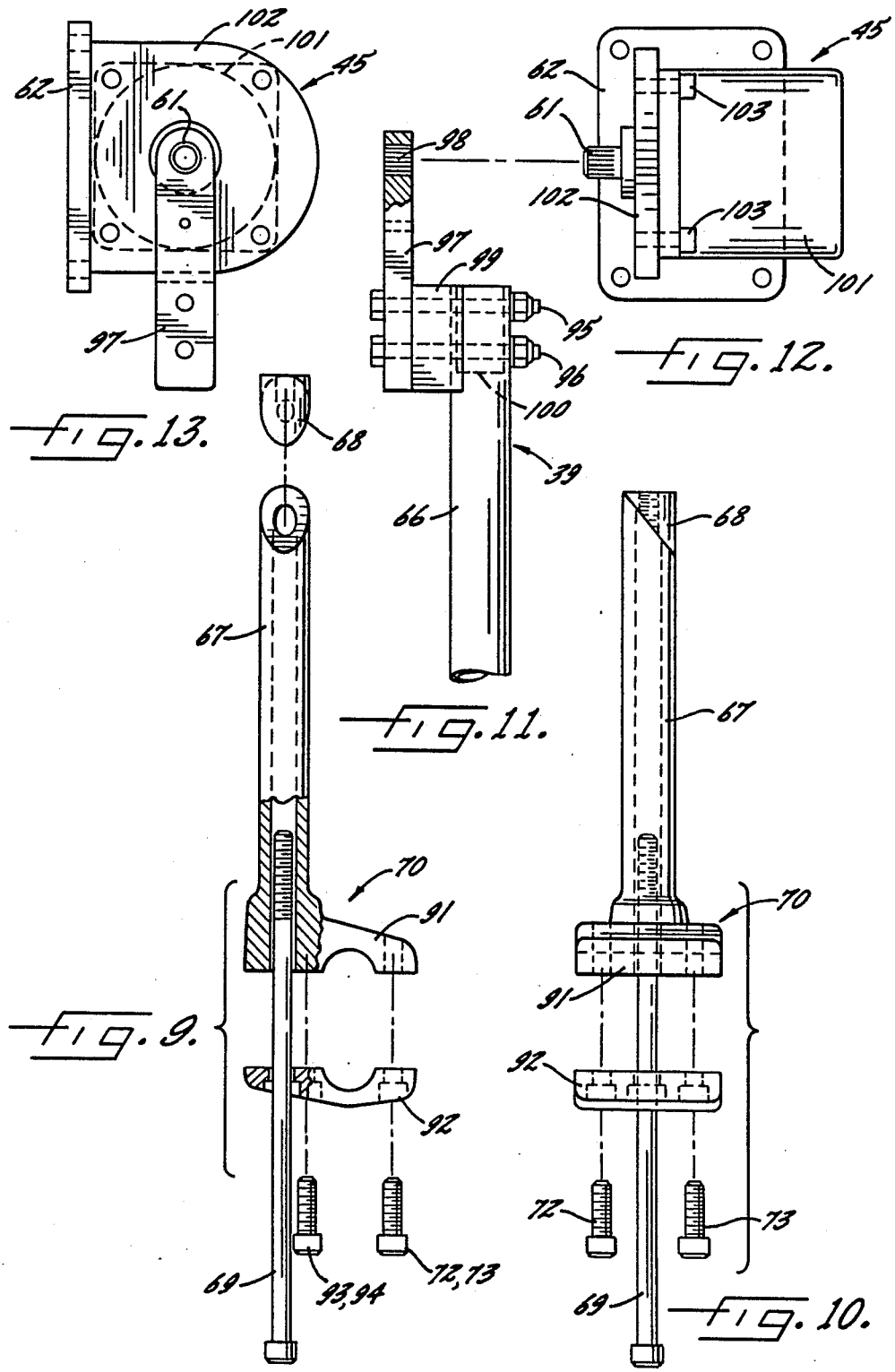

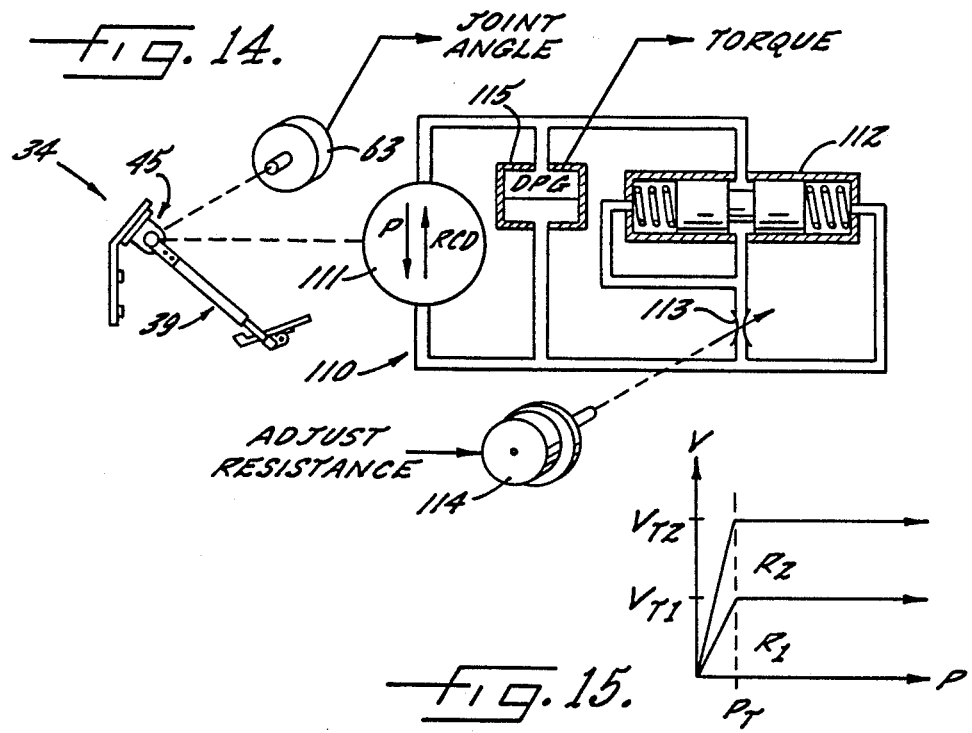
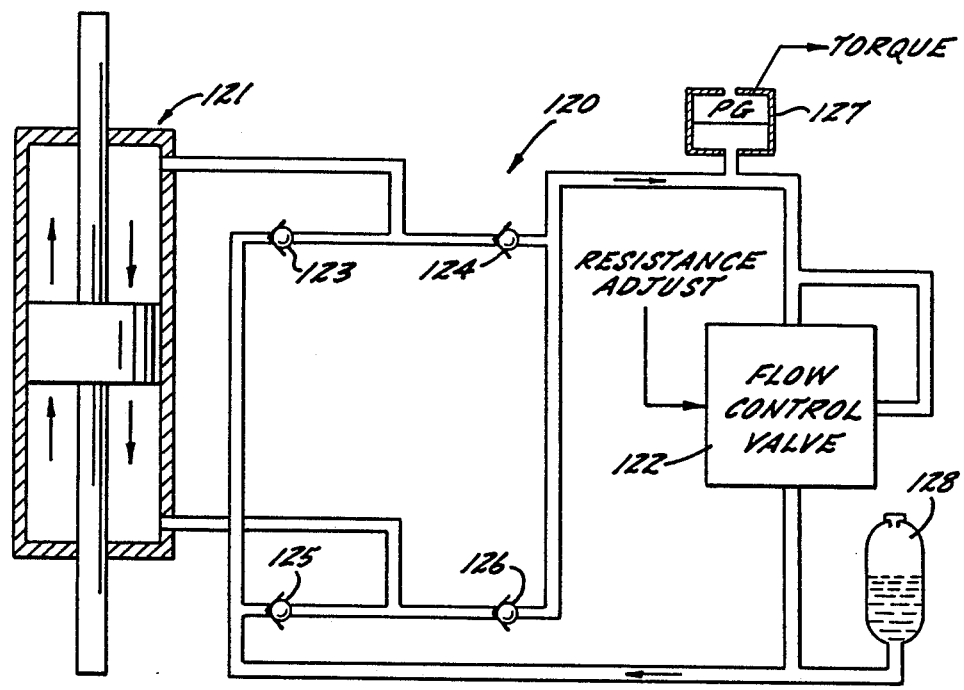

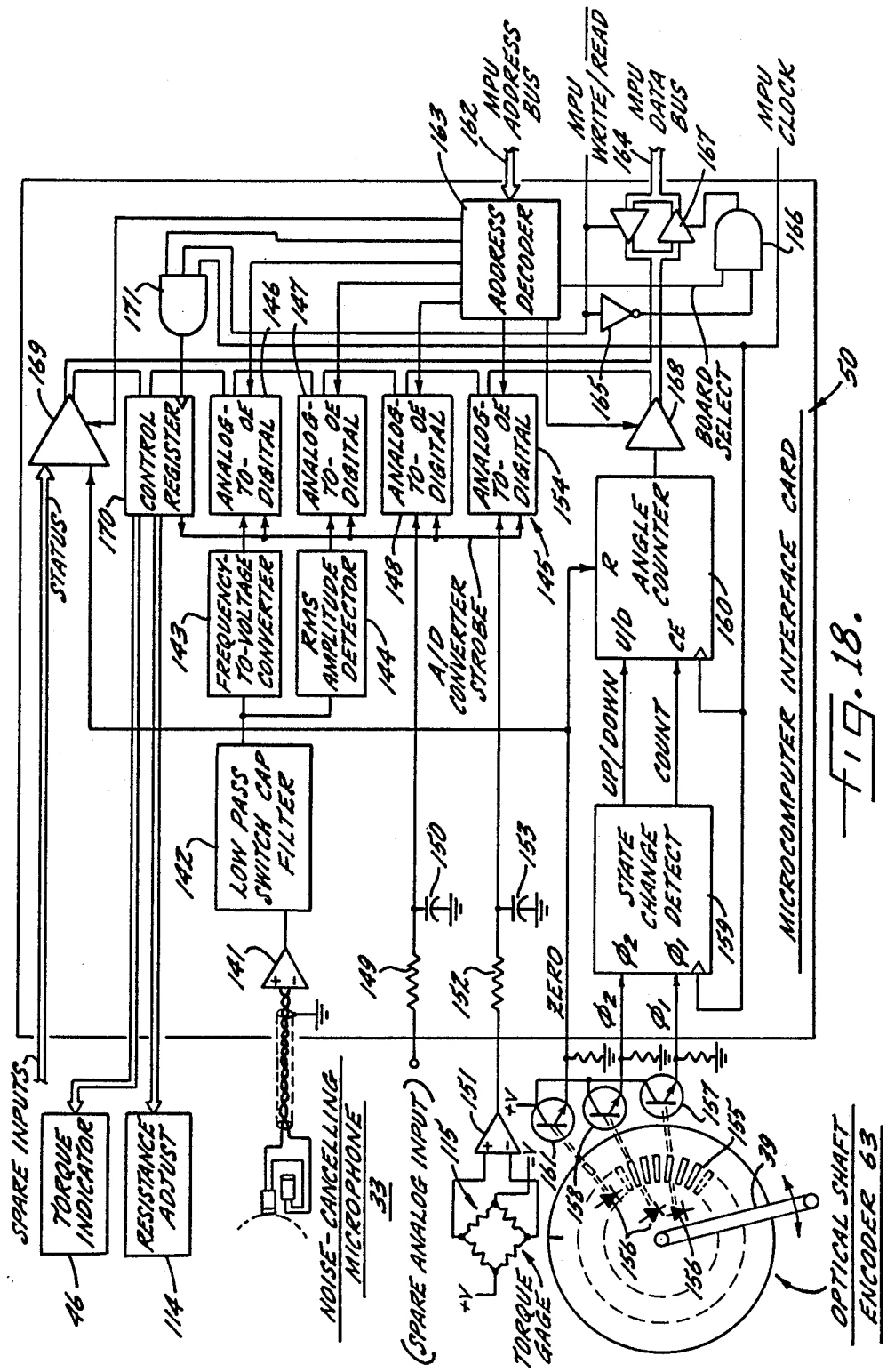

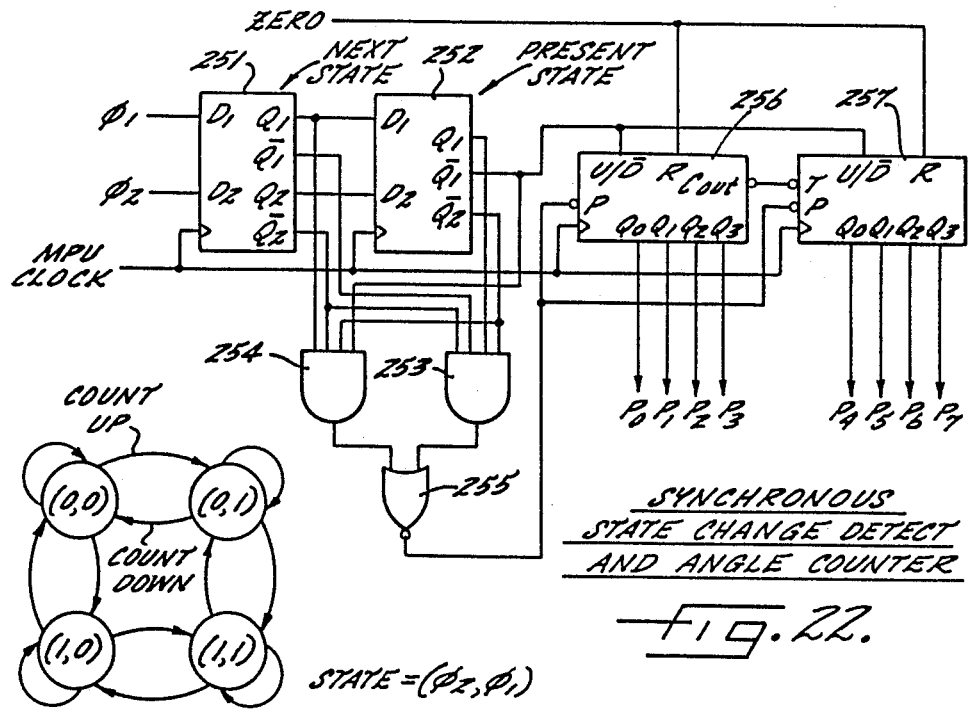
*SYNCHRONOUS STATE CHANGE DETECT AND ANGLE COUNTER*
Fig. 22.
*STATE DIAGRAM FOR ANGLE ENCODER*
Fig. 21.
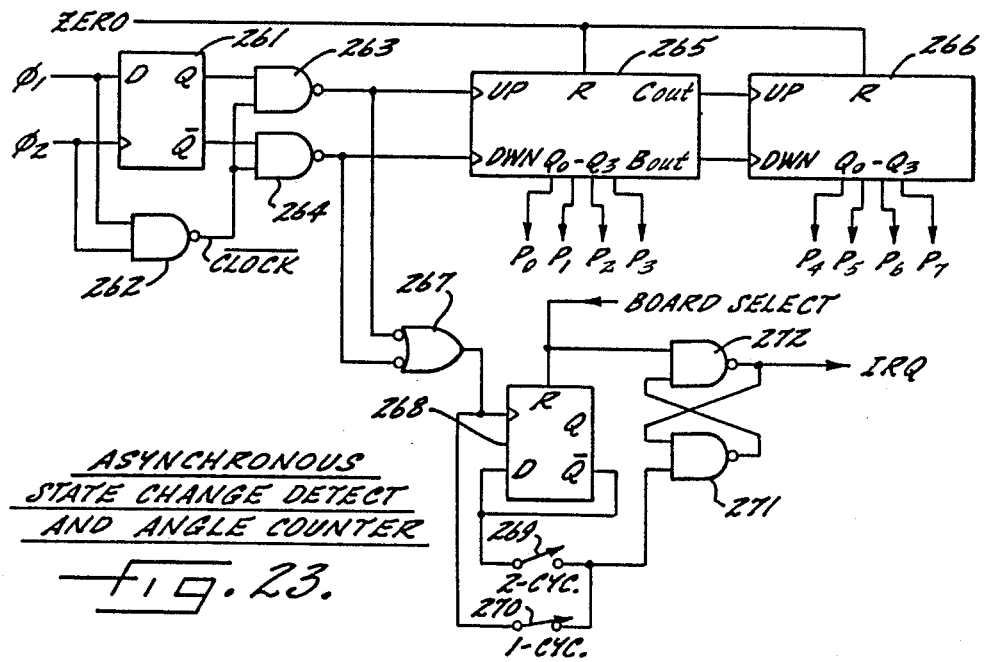
*ASYNCHRONOUS STATE CHANGE DETECT AND ANGLE COUNTER*
Fig. 23.

DEVICE FOR NON-INVASIVE DIAGNOSIS AND MONITORING OF ARTICULAR AND PERIARTICULAR PATHOLOGY

BACKGROUND OF THE INVENTION

1. Field of the Invention

The present invention relates generally to medical instrumentation, and more particularly to instrumentation for arthritis diagnosis. Specifically, the present invention relates to a device for the recording and analysis of sound emitted by the movement of human joints such as the knee.

2. Description of the Background Art

For at least 100 years, the crackling and grating sounds emitted by movement of arthritic knees have been considered during diagnosis. It was recognized that the motion of a diseased joint produces distinct sound waves or vibrations. But difficulties were encountered in distinguishing articular sounds from extrinsic sounds, such as noise due to snapping tendons, hand tremor, skin friction and other background noise.

It has only been in the last 10 years or so that instrumentation and methodology have been developed which may permit articular sound to be used as a reliable tool in the non-invasive identification of knee joint diseases. The instrumentation and methodology have been used primarily for research purposes, and are based upon the use of a noise cancelling microphone to pick up articular sounds relatively free from extrinsic sounds, and digital processing of the acoustic signal for recording, display and statistical analysis. The results of some of these research efforts have appeared in the medical literature.

Chu et al., "Detection of Knee Joint Diseases Using Acoustical Pattern Recognition Technique," *J. Biomechanics*, Vol. 9, pp. 111-114, 1976, discloses recording knee joint sound on magnetic tape during active movement of the knee. Background noise is minimized using the principle of "noise cancellation" thereby permitting analysis of what might be renamed an "acoustic signature." The signature is said to be the product of pattern recognition techniques applied to random noise. Studies of knee recordings covering normal, rheumatoid arthritic and degenerative knees are said to show that their respective waveforms, spectral patterns and statistical property of auto-correlation appear to be unique, and therefore, may well prove to be a promising non-invasive diagnostic tool for early detection of the type and extent of knee joint damage. A goniometer sensing the angle of the patient's knee joint was used to provide the horizontal sweep to an oscilloscope which displayed the acoustic signal; the waveform was captured by a polaroid camera. It was said that for the polaroid test, acoustical characteristics of waveform such as amplitudes, pulses and shapes are observed for the three different types of knee joint conditions, namely, normal, rheumatoid and degenerative cases.

Russell, "Clinical Utility of Acoustic Arthrography and Tendonography," Abstract, American Rheumatism Association, Annual Scientific Meeting, Anaheim, June 4-8, 1985, discloses that sounds produced by normal or rheumatic arthritic joints were recorded, stored in digital form, computer edited and printed graphically. Simultaneous video recording of joint motion allowed synchronization of mechanical and acoustic events. Flexion of rheumatoid knees exhibited higher (300 vs. 150 Hertz) peak sound frequencies with approximately twice the sound intensity as normal knees. The construction of a musculoskeletal acoustic data base is proposed.

"Noninvasive Test Can Distinguish Arthritic Joint by Noisy Movements," *Internal Medicine News*, Vol. 19, No. 11., p. 55, 1986 (citing Bol. Assoc. Med. P.R., 78:9-11, 1986), describes a rectifying-demodulating phonopneumograph developed by Dr. Casanova in which an acoustic signal from a transducer sensing joint crepitation is amplified, rectified, demodulated, and stored for visual analysis in an oscilloscope or with a chart recorder. Smooth contours were said to be frequently observed in patients with normal knee joints; curves characterized by multiple peaks occurred sometimes in normal and more often in arthritic joints. Sharp, brisk peaks were rarely seen in arthritic joints, and multiple peaks per wave were seen in both normal and arthritic joints on flexion or extension, but this pattern was more common in arthritic joints. Dr. Casanova's work is further reported in "Detecting Arthritis," *U.S. News and World Report*, p. 55, Aug. 18, 1986, which says that in a test with 19 people, a technique of amplifying sound vibrations made by joints in motion was 100 percent accurate in diagnosing eight patients with arthritis and eleven with normal joints.

While the above-described research efforts indicate that articular sounds can be used for diagnosing arthritis, the prior art instrumentation and methodology have not been applicable for routine diagnosis by the practicing physician due to the high cost of the instrumentation and the high degree of skill and judgment that has to be exercised by the physician in carrying out the methodology. In addition, the prior art instrumentation and methodology have not accurately simulated the conditions under which the human knee or other joint is subjected during normal daily life. The research efforts, however, evidence a long-felt need for an alternative to the exploratory arthroscopic surgery that has been the primary diagnostic technique employed by the practicing physician.

SUMMARY OF THE INVENTION

The primary goal of the present invention is to provide non-invasive instrumentation and methodology for use by the practicing physician for the routine diagnosis of arthritis.

Another object of the invention is to provide acoustic instrumentation and methodology for arthritis diagnosis at a minimum amount of expense and training of the diagnosing physician.

Still another object of the invention is to provide acoustic instrumentation and methodology for arthritis diagnosis under joint loading conditions which more accurately simulate the loading conditions experienced by the patient during daily life.

Yet another object of the invention is to provide acoustic instrumentation and methodology for arthritis diagnosis which employ a conventional "personal" microcomputer and pre-process the acoustic signal to determine both amplitude and instantaneous frequency so as to provide the practicing physician with real-time data analysis and display.

Briefly, in accordance with several important aspects of the present invention, arthritis and related diseases are diagnosed by recording sound or crepidence from a joint moving against a predefined resistance, and correlating the acoustic amplitude and instantaneous frequency with the joint angle. The record of acoustic amplitude and frequency as a function of the joint angle provides an "acoustic arthrograph" which can be analyzed statistically and easily compared to previous recordings that have been classified according to the type and severity of joint disease.

A preferred apparatus of the invention includes an articulated restraint for receiving a limb, a position sensor for sensing the joint angle, a hydraulic unit including a rotary actuator or double-ended piston and a flow regulator valve for applying a predetermined resistance to joint movement, a pressure gage for measuring the torque about the joint, a noise cancelling microphone or accelerometer for sensing joint crepidence, an amplifier and filter for selecting the acoustic signal representing crepidence, a frequency-to-voltage converter for detecting the instantaneous frequency of the crepidence signal, an amplitude detector for detecting the amplitude of the crepidence signal, an analog-to-digital converter for obtaining simultaneous numerical samples of the instantaneous frequency, amplitude, and torque; and a computer for recording and processing the numerical samples.

DESCRIPTION OF THE DRAWINGS

Other objects and advantages of the invention will become apparent upon reading the following detailed description and upon reference to the drawings in which:

FIG. 3 is a top view of an articulated leg restraint used during the examination depicted in FIG. 1;

FIG. 4 is a front view of a foot support assembly of the articulated leg restraint;

FIG. 5 is a front view of a horizontal support rod and bearing retainer used in the foot support assembly of FIG. 4;

FIG. 6 is a front view of a spindle, clamp and clamping knob used in the foot support assembly of FIG. 4;

FIG. 7 is a bottom view of the foot support assembly;

FIG. 8 is a bottom view of the horizontal support rod and bearing retainer of FIG. 5;

FIG. 9 is a side view of a clamp for connecting the horizontal support rod to a swinging arm, the clamp being mounted on a rod providing the swinging arm with an adjustable length;

FIG. 10 is a front view of the clamp of FIG. 9;

FIG. 11 is a front view of the swinging arm;

FIG. 12 is a front view of a hydraulic unit with the swinging arm removed;

FIG. 13 is a side view of the hydraulic unit showing its connection to the swinging arm;

FIG. 14 is a schematic diagram of a simplified fluid circuit for the hydraulic unit;

FIG. 15 is a graph of fluid velocity versus pressure in the hydraulic circuit of FIG. 14;

FIG. 16 is a preferred fluid circuit for the hydraulic unit;

FIG. 18 is a block diagram of a microcomputer interface circuit for interfacing the articulated leg restraint of FIG. 1;

FIG. 21 is a state diagram for an angle encoder having a pair of quadrature outputs;

FIG. 22 is a detailed schematic diagram of synchronous logic for detecting the change of state of the angle encoder and counting up or down to indicate angular position;

FIG. 23 is an alternative circuit which uses asynchronous logic for detecting the change in state of the angle encoder and counting up or down to indicate angular position;

Figure 1:
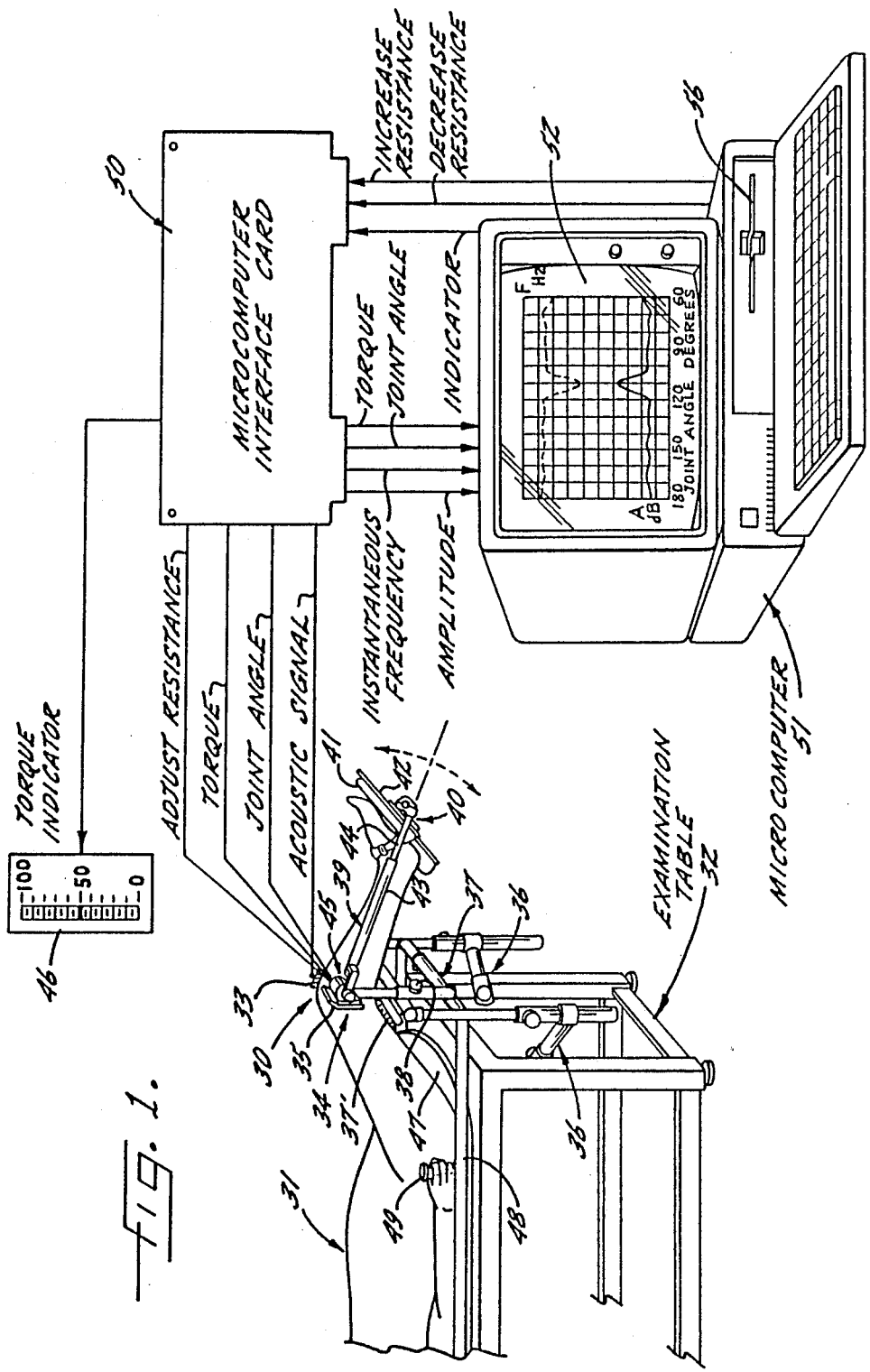
FIG. 1 is a schematic diagram showing the invention being used to examine a patient for signs of disease in the right knee.

While the invention is susceptible to various modifications and alternative forms, specific embodiments thereof have been shown by way of example in the drawings and will herein be described in detail. It should be understood, however, that it is not intended to limit the invention to the particular forms disclosed, but on the contrary, the intention is to cover all modifications, equivalents and alternatives falling within the spirit and scope of the invention as defined by the appended claims.

DESCRIPTION OF THE PREFERRED EMBODIMENTS

Turning now to the drawings, there is shown in FIG. 1 a preferred embodiment of the present invention being used to examine the right knee 30 of a patient 31 lying on an examination table 32. It is known that certain kinds of joint disease cause a moving joint to emit characteristic sounds. In order to sense these sounds, a noise cancelling microphone 33 is secured to the knee by adhesive tape. The technique of mounting such a noise cancelling microphone to obtain acoustic signals is well known in the art and is described in Chu et al., "Detection of Knee Joint Diseases Using Acoustical Pattern Recognition Technique," *J. Biomechanics* Vol. 9, pp. 111-114, 1976, herein incorporated by reference. It has also been found that an accelerometer can be used in lieu of a noise cancelling microphone to sense the acoustic signals emitted by the knee or other joint. A suitable accelerometer is a model 502-1 sold by Metrix Instruments Co., Houston, Tex.

In accordance with an important aspect of the present invention, the acoustic signal is obtained under controlled conditions which permit more accurate diagnosis and permit any change in the patient's condition to be more precisely detected. These controlled conditions are established by an articulated leg restraint 34 which applies a controlled resistance and establishes a controlled velocity during movement of the knee 30. The controlled resistance or velocity causes forces to occur in the knee that are comparable to the forces occurring when the patient walks up a flight of stairs.

The articulated leg restraint 34 includes a base member 35 which is clamped to the examination table 32 by moveable post sockets or adjustable stirrup holders 36 which are present on the examination tables typically used in doctors' offices As shown in FIG. 1, for example, a pair of stirrup holders 36 are secured to the table 32, and there is a rectangular frame 37 having legs received in the stirrup holders 36. A pad 37' is mounted to the top of the rectangular frame 37 for supporting the patient's thighs. The base member 35 is clamped to the rectangular frame 37 via an adjustable clamp 38. Therefore, the height of the base member 35 is readily adjustable with respect to the examination table 32.

In order to track the flexion and extension of the knee 30, the articulated leg restraint 34 includes a swinging arm 39 which is pivotally attached to the base member 35. In practice, the clamp 38 is adjusted so that the axis of the patient's knee 30 coincides with the pivot axis of the swinging arm 39. This is done, for example, by first positioning the patient on the examination table so that the axis of the knee is a predefined distance horizontally from the examination table 22. As shown, the patient 31 is placed in a lying or recumbant position with his or her hip fixed at a certain distance from the end of the examination table 32. Then the base member 35 is raised and clamped at the required height. Next, a foot support assembly 40 is adjusted to provide a support for the patient's foot, and the patient's foot is strapped into a sandal 41 attached to a foot plate 42 of the foot support assembly 40. In this regard, the swinging arm 39 is comprised of two telescoping sections 43 and 44 which permit the length of the swinging arm 39 to be adjusted in accordance with the length of the patient's leg.

In accordance with another important aspect of the present invention, the resistance to motion of the patient's knee is provided by a hydraulic unit generally designated 45 which permits precise adjustment of the resistance to obtain substantially constant velocity of angular movement. In addition, the hydraulic unit 45 includes a pressure sensor which indicates the torque on the patient's knee 30 provided by the resistance. By using a torque indicator 46 to indicate the torque to the patient 31, the patient can be requested to exert a sufficient amount of muscular force to keep the torque at a constant value. Therefore, the hydraulic unit 33 in connection with the torque indicator 46 permits the acoustic signal to be sensed under the conditions of a constant predetermined velocity and a constant predetermined torque or resistance.

In order to provide comparisons of the acoustic signal, the hydraulic unit 45 has associated with it a sensor for sensing the angular position of the swinging arm 39 with respect to the base member 35. Since the pivot of the swinging arm 39 is aligned with the axis of the knee, this sensor indicates the angle of the patient's knee. Therefore, by associating the acoustic signal with the sensed angle, it is possible to precisely compare the acoustic signal to the signals obtained during previous examinations.

Although the articulated leg restraint 34 is particularly useful for diagnosing joint disease or damage, it is also useful as a tool for judging the strength of the knee in the practice of sports medicine. In this case, it could be desirable to immobilize the patient with respect to the frame 37 by placing the patient on a plastic seat and back support 47 secured to the rectangular frame 37 via horizontal side bars 48 which rest on the top of the examination table 32. The horizontal side bars 48 could have handles 49 protruding vertically for the patient to grasp.

In accordance with another important aspect of the present invention, there is provided a microcomputer interface circuit generally designated 50 which can be used to interface the articulated leg restraint 34 to a conventional microcomputer 51. Preferably the interface circuit resides on a single printed circuit card which can be inserted into the card cage of the microcomputer. As shown in FIG. 1, for example, the microcomputer is compatible with an IBM PC XT or AT computer. The interface circuit 50 performs analog pre-processing of the acoustic signal and thereby greatly reduce the real-time processing requirements of the microcomputer 51. In practical terms, this permits the microcomputer 51 to immediately display the instantaneous frequency and amplitude of the acoustic signal during movement of the patient's knee. As shown in FIG. 1, for example, the interface circuit 50 transmits to the microcomputer numerical values to indicate the torque, joint angle, instantaneous frequency, and amplitude of the acoustic signal emitted by the patient's knee. In addition, the microcomputer 51 may transmit commands to command the interface circuit 50 to increase or decrease the resistance and to cause the indicator 46 to indicate a particular level of torque.

Figure 2:
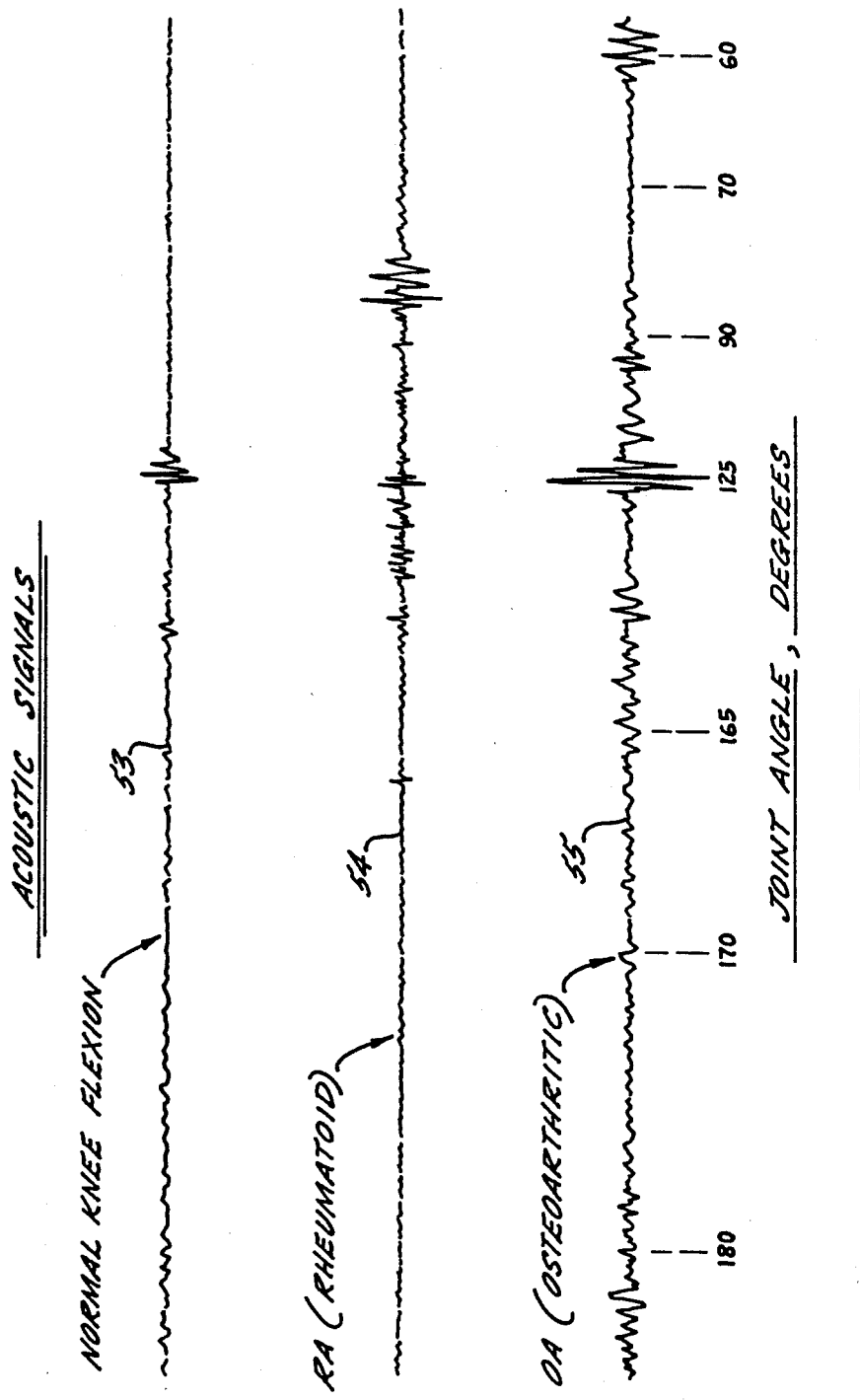
FIG. 2 shows typical acoustic signals emitted during movement in a normal knee, a rheumatoid knee, and an osteoarthritic knee.

As specifically shown in FIG. 1, the microcomputer 51 is connected to a cathode ray tube display monitor 52 which has plotted the angle, frequency and amplitude of acoustic signals emitted during flexion or extension of the knee. It should be noted that for a normal knee in which disease is absent the acoustic signals will have a relatively low and constant amplitude, and will have a relatively high and constant instantaneous frequency. This should be apparent from inspection of the acoustic signal 53 for normal knee flexion as shown in FIG. 2. The acoustic signal 54 for a rheumatoid knee exhibits an increased amplitude and a slightly lower frequency. The acoustic signal 54 for an osteoarthritic knee, on the other hand, exhibits an even greater increase in amplitude and a substantial decrease in instantaneous frequency. Therefore, the graphs on the display 52 of the microcomputer 51 provide a concise summary of the characteristics of the acoustic signal which serve to distinguish the normal knee from the two disease damaged knees, and further appears to distinguish the two major cases of joint disease.

At the end of flexion or extension of the knee, the amplitude and instantaneous frequency for various increments of joint angle, for example for every degree, are stored as arrays of data values in the microcomputer 51. These array of data values are preferably stored on a magnetic disk in one of the disk units 56 of the microcomputer. The data arrays are preferably associated with other data about the patient so as to provide a data base which eventually will enable the computer to automatically diagnose joint disease and indicate its severity by applying standard pattern recognition techniques. Such techniques are described, for example, in George S. Sebestyen, *Decision-Making Processes In Pattern Recognition,* The MacMillian Company, New York, (1962). in general, these pattern recognition techniques treat the data for a single flexion or extension of the leg as a pattern vector, and compute the difference between the pattern vector and each of a number of predetermined vectors, each of which is associated with a predetermined condition. The pattern vector for the test is then associated with or recognized as belonging to the same class as the predetermined pattern vector for which the magnitude of the difference is a minimum.

Turning now to FIG. 3, there is shown a plan view of the articulated leg restraint 39 and the hydraulic unit 45. The hydraulic unit 45 has a shaft 61 which pivotally mounts the swinging arm 39 to the base 62 of the hydraulic unit. To sense the angular position of the swinging arm 39, an angle sensor 63 is aligned coaxially with the shaft 61 and is mounted to the base 62 by a bracket 64. The angle sensor 63 is preferably an optical encoder having a pair of quadrature outputs, although a simple potentiometer could be used instead. Alternatively, the angle sensor could be built inside the hydraulic unit, as further described below in connection with FIGS. 17A and 17B. The angle sensor 63 has an input shaft or lever 65 which is fastened to the swinging arm 39. Therefore, the input shaft or lever 65 tracks the swinging motion of the arm 39.

In order to adjust the length of the arm 39 to accommodate the length of the patient's leg, the body of the arm is provided by a tube 66 which telescopingly receives a rod 67 having a split end portion 68 for clamping the rod 67 inside the tube 66. For this purpose the end portion 68 is wedge-shaped and is threaded to receive the end portion of a clamping bolt 69.

To permit adjustment of the angle of the foot support plate 62 relative to the swinging arm 39, the rod 67 is welded or otherwise secured to a clamp 70 which receives a horizontal support rod 71 to which the foot support assembly 40 is mounted. The clamp 70 includes clamping screws 72 and 73 which may be loosened to permit the horizontal support rod 71 to rotate and may permit adjustment of the distance from the foot support plate 42 to the swinging arm 39. Once the desired position is obtained, the clamping screws 72, 73 are tightened to fix the position of the foot support plate 42 with the respect to the swinging arm 39.

A front view of the foot support assembly 40 is shown in FIG. 4. To permit the foot support plate 42 to be rotatably adjusted with respect to the horizontal support rod 71, the foot support plate is pivotally mounted to a bearing retainer 74 which is attached by screws 75 and 76 to the end portion of the horizontal support rod 71. The foot support plate 42 is secured by screws 77 and 78 to a spindle generally designated 79. The spindle 79 is made up of an annular ring 80 and disk 81. The disk 81 has a central hole for receiving a bolt 82 which is secured to the disk 81 by a nut 83. During assembly, a bearing 84 is interposed between the bearing retainer 74 and the nut 83. The bolt 82 is itself secured to the bearing retainer 74 by a nut 85 and a washer 86. The nut 85 is only tightened as much as required to eliminate play between the nut 83 and the bearing retainer 74. Therefore, the foot support plate 42 is relatively free to rotate with respect to the horizontal support rod 71 about the axis of the bolt 82. To fix the angular position of the foot support plate 42, there is provided a clamp 87 which clamps the disk 81. The clamp 87 is mounted to a rectangular plate 88 which is welded to the horizontal support rod 71. The clamp 87 includes a threaded stud 89 which passes through a hole in the rectangular plate 88 and is threaded to a clamping knob 90. As is more clearly shown in FIG. 7, the clamp 87 and clamping knob 90 are offset with respect to the horizontal support rod 71.

Turning now to FIG. 9 and 10, there is shown the clamp 70 for clamping the horizontal support rod 71 to the swinging arm 39. The clamp 70 includes an upper portion 91 welded or otherwise secured to the rod 67, and a lower portion 92 which is secured to the upper portion by four bolts 72, 73, 93 and 94.

The upper portion of the swinging arm 39 is shown in FIG. 11. The upper end of the tube 66 is secured by bolts 95 and 96 to an extension 97 having an aperture 98 for receiving the shaft 61 of the hydraulic unit 45. The tube 66 is offset from the extension 97 by a spacer 99. To prevent the upper portion of the tube 66 from collapsing when the bolts 95 and 96 are tightened, a cylindrical spacer 100 is inserted inside the upper portion of the tube 66.

The hydraulic unit 45 is shown in FIG. 12. The shaft 61 extends to a hydraulic rotary actuator 101 which is, for example, a "Rotac" (registered trademark) torque actuator. The actuator 101 is mounted to the base 62 by four screws 103 which engage a bracket 102 welded to the base 62.

Turning now to FIG. 14, there is shown a schematic diagram of the articulated leg restraint 34 including the hydraulic unit 45 and a simplified hydraulic circuit generally designated 110 which provides a controlled resistance to relative motion of the swinging arm 39. The hydraulic unit 35 includes a reversible pump 111 which pumps hydraulic fluid in response to the relative motion of the swinging arm 39. The pump 111 could be provided by a rotary actuator 101, as shown in FIGS. 1, 3, 12 and 13, or it could be provided by a double-ended piston and cylinder 121, as shown below in FIGS. 16 and 17A to 17C.

The pump provides substantially constant displacement of hydraulic fluid through the hydraulic circuit 110. The circuit 110, however, includes a flow regulator valve 112 which maintains a substantially constant flow through an adjustable orifice or needle valve 113. As shown, the flow regulator valve is a spool valve which is centered with respect to inlet and outlet ports when there is no pressure across the needle valve 113. However, when the pressure across the needle valve exceeds a predetermined threshold, the spool valve becomes closed. Therefore, the displacement or flow of hydraulic fluid through the circuit is limited to a predetermined value set by the pressure threshold of the regulator valve 112 and the resistance of the needle valve 113.

As shown graphically in FIG. 15, the resistance to fluid flow increases sharply when the flow causes the pressure threshold $P_T$ of the regulator valve 112 to be exceeded. Therefore, the velocity of the swinging arm 39 will be limited to a predetermined velocity which can be set by adjusting the needle valve 113. The microcomputer (51 in FIG. 1) can do this automatically by operating a stepper motor 114. Specifically, the microcomputer first drives the stepper motor to a limit stop position wherein the needle valve is closed, and then steps the stepper motor a predetermined number of steps in the opposite direction to open the needle valve a sufficient amount to obtain a desired velocity limit. The microcomputer, for example can obtain the predetermined number of steps for a desired velocity limit from a prestored calibration table. In general, it is desirable to adjust the velocity limit to maximize the amplitude of the acoustic signal emitted by the joint under investigation. For a knee, this typically occurs when the knee moves 120° in about one to two seconds.

In order to sense the torque applied by the swinging arm to the patient's knee due to the resistance, a differential pressure gage 115 may be used to sense the pressure provided by the pump 111. As is well known, a differential pressure gage includes a metal diaphragm and a strain gage bonded to the diaphragm for sensing the deformation of the diaphragm due to a differential pressure. Alternatively, the differential pressure could be sensed by two unidirectional pressure gages which are electrically wired in a differential circuit. Suitable strain gages are provided in the *OMEGA Pressure and Strain Measurement Handbook and Encyclopedia*, OMEGA Engineering, I OMEGA Drive, Box 4047, Stamford, CT 06905 (1985).

It should be apparent that the microcomputer can automatically calibrate the needle valve 113 to obtain a desired velocity threshold. The microcomputer, for example, has a real time clock which can be used to compute the angular velocity of the swinging arm 39 as the change in angular position divided by the change in time. The microcomputer can also read the torque or pressure to determine whether the pressure is substantially in excess of the pressure threshold $P_T$, and if this is the case, then the microcomputer may increase or decrease the resistance of the needle valve 113 by an amount proportional to the error between the sensed angular velocity of the swinging arm and the desired angular velocity of the swinging arm. Therefore, by this feedback technique, the microcomputer can continue adjusting the needle valve until the desired angular velocity is obtained.

Turning now to FIG. 16, there is shown a preferred hydraulic circuit 120 for using a conventional pressure-compensated unidirectional flow control valve 122. A double-ended hydraulic piston and cylinder 121 is shown as being used as a reversible pump in the circuit 120. The piston and cylinder assembly 121 preferably has a diameter of 1 to 1.5 inches and a throw of about 4 inches. A matrix of four check valves 123, 124, 125, 126 provide a unidirectional hydraulic path from the cylinder 121 to the flow control valve 122. The flow control valve 122 is, for example, part no. 2FRM5-31-6Q sold by Rexroth Corporation. A unidirectional pressure sensor 127 is used for sensing the torque or force applied to the piston and cylinder assembly 121. A hydraulic reservoir 128 insures that the return pressure is substantially at atmospheric pressure, so that a differential pressure sensor is not needed to accurately measure the torque.

Figure 17C:
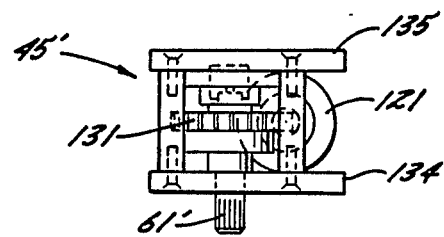
FIGS. 17A, 17B and 17C are front, rear and top views of an alternative hydraulic unit which uses a double-ended piston and cylinder assembly.
Figure 17B:
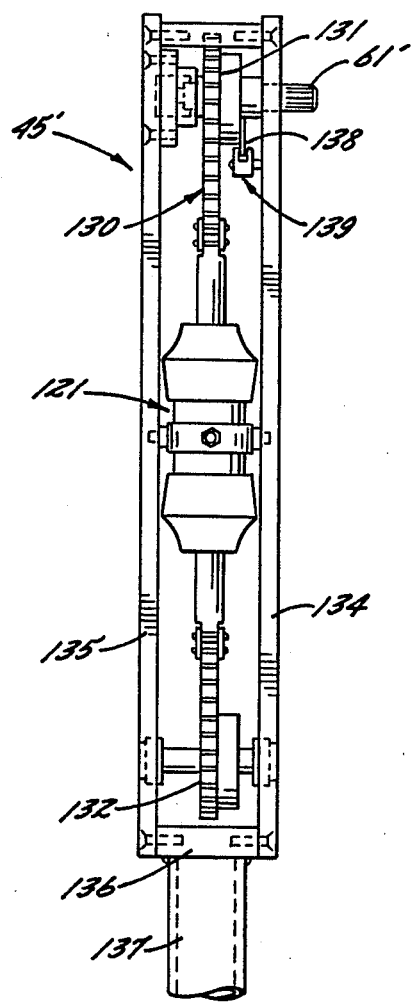
Figure 17A:
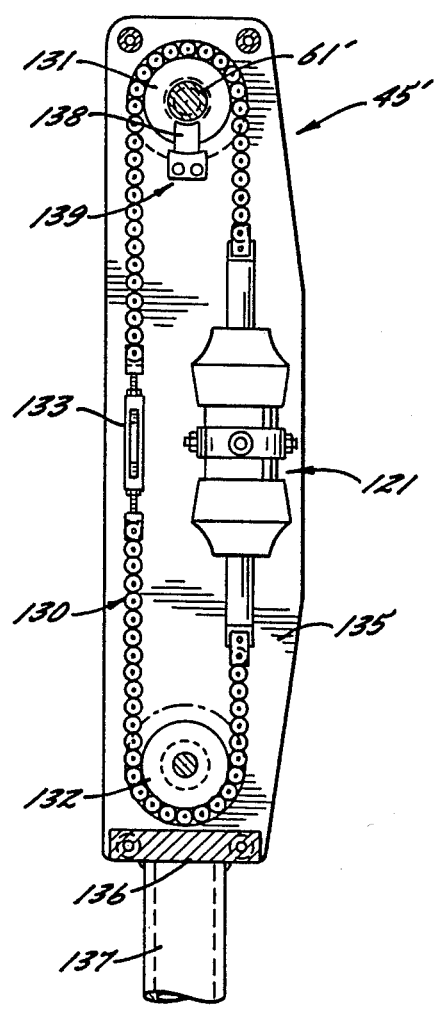

Turning now to FIGS. 17A to 17C, there are shown an inside front view, a rear view, and a top view of an alternative hydraulic unit 45' which uses the double-ended piston and cylinder assembly 121 instead of a rotary actuator. The hydraulic unit 45' includes a chain 130 and sprockets 131 and 132 for converting the rotary motion of a shaft 61' to the rectilinear motion of the piston and cylinder assembly 121. The shaft 61' is attached to the swinging arm 39 (not shown) and the sprocket 131 is also attached to the shaft 61'. The second sprocket 132 is an idler sprocket. A turnbuckle 133 insures that the chain is tight to prevent "play" between the rotation of the shaft 61' and the translation of the piston in the assembly 121.

In order to mount the hydraulic unit 45' to the examination table (32 in FIG. 1), the sprockets 1 31, 132 are journaled to side plates 134, 135 between which the piston and cylinder assembly 121 is sandwiched. The lower end portions of the side plates are screwed to a base plate 136 welded to a mounting rod 137. The mounting rod would be received in the frame 37 of FIG. 1 and clamped at a selected height by the clamp 38.

As illustrated in FIGS. 17A and 17B, an angle position sensor can be formed inside the hydraulic unit 45'. For this purpose an optically coded disk 138 could be secured to a shoulder on the shaft 61', and a sensor device 139 could sense the optically coded disk. The operation of such a position detector will be more fully described below in connection FIG. 18 and FIGS. 21–23.

Turning now to FIG. 18, there is shown a block diagram of the microcomputer interface circuit 50. In order to select the acoustic signal from the microphone or accelerometer 33 which indicates sound from the patient's knee, the signal from the microphone or accelerometer is isolated or amplified by an amplifier 141 and filtered by a low pass filter 142. The low pass filter is preferably a switched capacitor filter having a sharp 2kHz cutoff frequency. The filtered signal is supplied to a frequency-to-voltage converter 143 and a RMS amplitude detector 144. The amplifier 141, low pass filter 142, frequency-to-voltage converter 143, and RMS amplitude detector 144 are further described below in connection with FIG. 19.

In order to provide the microcomputer with numerical values representing the instantaneous frequency and amplitude of the acoustic signal, there is provided an analog-to-digital converter generally designated 145 which preferably includes a separate integrated analog-to-digital converter for each of a number of analog inputs. Alternatively, a single fast analog-to-digital converter could be used with an analog multiplexer to nearly simultaneously sample a number of analog inputs. However, due to the relatively low cost of integrated analog-to-digital converters, it is preferable to use a separate analog-to-digital for each analog input. The analog-to-digital converters are, for example, National Semiconductor part number AD0820. An analog-to-digital converter 146 is provided for sampling the frequency indicating signal from the frequency-to-voltage converter 143 and a second analog-to-digital converter 147 is provided for sampling the amplitude signal from the amplitude detector 144. In addition, there is provided a third analog-to-digital converter 148 for sampling a space analog input through a simple low-pass filter including a resistor 149 and a capacitor 150. The resistor 149, for example, has a value of 10K ohms, and the capacitor 150 has a value of 0.01 microfarads. The spare analog input for example, could be used for a potentiometer which senses the angular position of the swinging arm 39.

In order to provide numerical samples indicating the torque applied to the patient's knee, the torque gage 115 has a bridge circuit of sensor elements, and a strain causes the bridge to become unbalanced. The differential signal across the bridge is amplified by a differential amplifier 151 and the amplified difference signal is fed through a simple low-pass filter including a resistor 152 and a capacitor 153. The resistor 152, for example, has a value of 10K ohms and the capacitor 153 has a value of 0.05 microfarads. The signal from this low-pass filter is fed to an analog-to-digital converter 154.

In order to sense the angular position of the swinging arm 39, the optical shaft encoder 63 has an optically encoded disk 155 which has, for example, a pattern of optically transparent slits, each slit being one-half degree in width and the center each slit being spaced by one degree from the center of an adjacent slit. Light emitted by a pair of light-emitting diodes 156 pass through the slit and are received by respective phototransistor 157, 168 which are spaced from each other by one-quarter of a degree, or 90° in phase with respect to the wavelength of the pattern of optically transparent slits on the encoded disk 155. Therefore, the phototransistors 157, 158 provide quadrature signals $\phi_1$ and $\phi_2$. These quadrature signals are fed to a state change detector circuit 159 which detects whether the swinging arm 39 changes its position in the clockwise or counterclockwise direction. In response to an angular change, the state change detector 159 provides signals to increment or decrement an angle counter 160. As shown in FIG. 18, the state change detector 159 and angle counter 160 operate synchronously with the microcomputer's clock. Suitable synchronous circuits are shown and described below in connection with FIG. 22. Alternatively, an asynchronous circuit could be used as shown and described below in connection with FIG. 23. In order to define a zero position for the swinging arm 39, the optical shaft encoder 63 has a third phototransistor 161 which generates a zero pulse when the swinging arm 39 is at a predefined zero position. This zero pulse is used to reset the angle counter 160.

In order to permit the microcomputer to read a selected one of the analog-to-digital converters or to read the angle counter 160, the microcomputer addresses the interface circuits through an address bus 162 which is fed to an address decoder 163. When the interface circuits 50 are addressed, the address decoder 163 generates a board select signal which enables data to be passed from the interface circuits to a microcomputer data bus 164 when the microcomputer is performing a read operation as indicated by a WRITE/READ signal. For this purpose, the interface circuits 50 include an inverter 165 and an AND gate 166 which enables a tri-state driver 167 for asserting data on the data bus 164. The data to be transmitted is further selected by more specific outputs of address decoder 163. For example, the address decoder 163 may enable the outputs of a particular one of the analog-to-digital converters 146, 147, 148 or 154. In addition, the address decoder may enable a set of tristate gates 168 for transmitting the value of the angle counter 160.

In order to detect that the angle counter has been properly reset by the zero signal from the angle encoder 63, the interface circuits 50 include a status register or set of tri-state gates 179 which can be enabled by a respective output of the address decoder 163.

It is also desirable to permit the microcomputer to output data to the interface circuits 50. For this purpose there is provided a control register 170 for receiving data from the microcomputer data bus 164. The control register is a set of eight delay flip-flops which are clocked by a write pulse from an AND gate 171. The AND gate 171 receives the microcomputer clock, the WRITE/READ signal and a respective output from the address decoder 163. The control register 170 has a single bit output for strobing or simultaneously activating the analog-to-digital converters to sample and hold their analog inputs. The control register 170 has additional bits, including three of which may be used for operating the stepper motor 114 to adjust the resistance provided by the hydraulic unit (FIG. 14) and four bits which could be used to drive the torque indicator 46 (FIG. 1). The circuits for driving the stepper motor 114 and the torque indicator 46 are shown and further described below in connection with FIG. 24.

Figure 19:
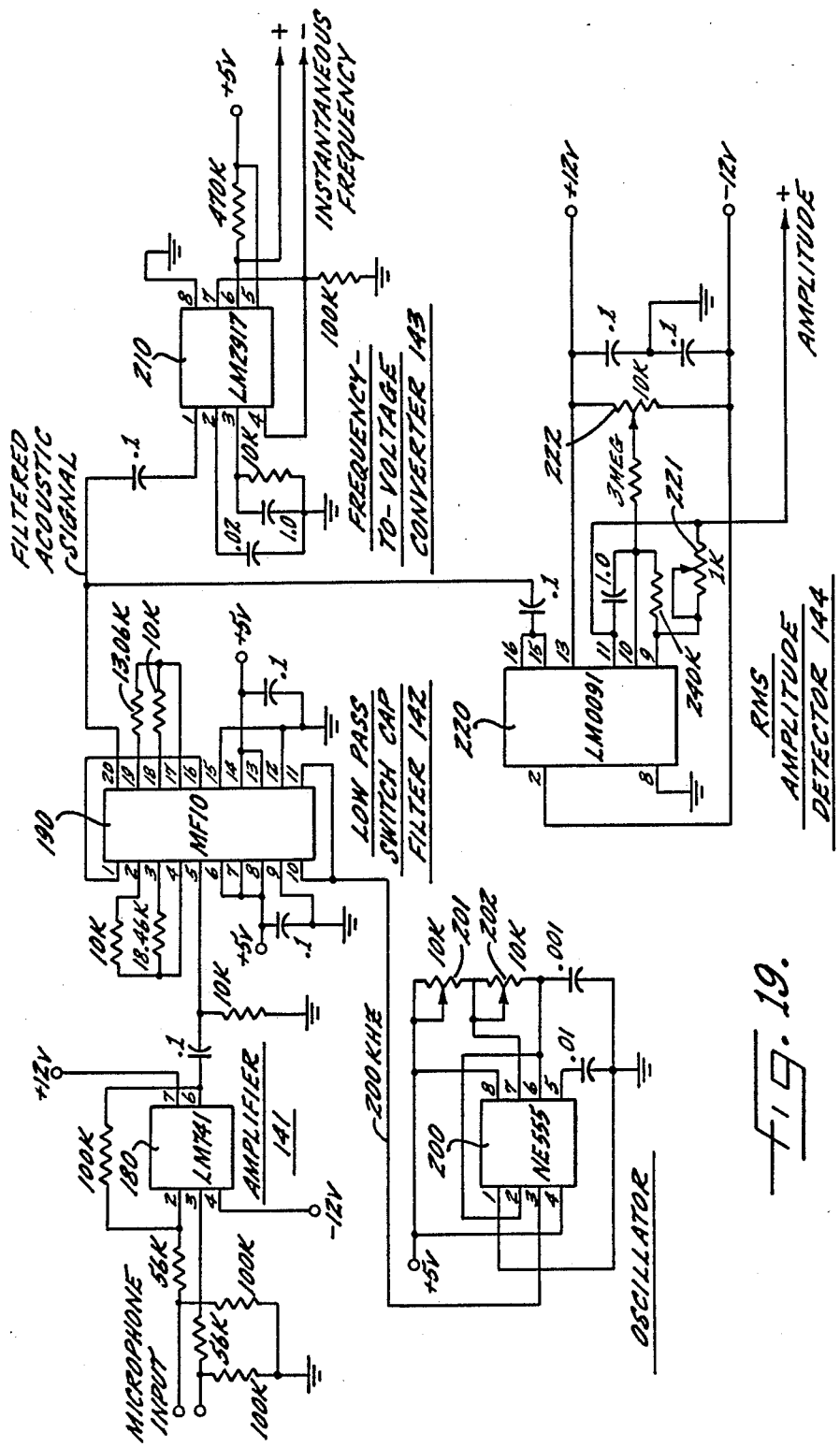
FIG. 19 is a detailed schematic diagram of circuits for obtaining the instantaneous frequency and amplitude of an acoustic signal.

Turning now to FIG. 19, there are shown preferred circuits for the amplifier 141, the low pass filter 142, the frequency-to-voltage converter 143, and the RMS amplitude detector 144. The amplifier 141 includes an operation amplifier integrated circuit 180 which is part no. LM741. On the drawing in FIG. 19, the pins of the operational amplifier 181, as well as the other integrated circuits, are numbered with their physical lead or pin numbers. Also shown in FIG. 19 are the associated resistors and capacitors which are used in connection with the integrated circuits. These resistors and capacitors are labeled with their component values. The resistor values are in ohms unless otherwise indicated, and the capacitor values are in microfarads unless otherwise indicated.

The low pass filter 142 is provided by a switched capacitor low pass filter integrated circuit 190, part no. MF10. The cut-off frequency of the switched capacitor filter 142 is determined by a 200 kHz clock from a timer integrated circuit 200, part no. NE555. The precise cut-off frequency, however, is adjustable by an adjustable 10K ohm resistor 201 and an adjustable 5K ohm resistor 202.

The filtered acoustic signal is fed to the frequency-to-voltage converter 143 and also to the RMS amplitude detector 144. The frequency-to-voltage converter 143 uses an integrated circuit 210 which is part no. LM2917. The RMS amplitude detector 144 uses an integrated circuit 220 which is part no. LM0091. The "gain" and the "zero" of the RMS amplitude detector 144 are adjustable by respective adjustable resistors 221 and 222. The RMS amplitude detector 144 operates in a similar fashion to a diode rectifier or envelope detector, except that it is somewhat more accurate.

Figure 20:
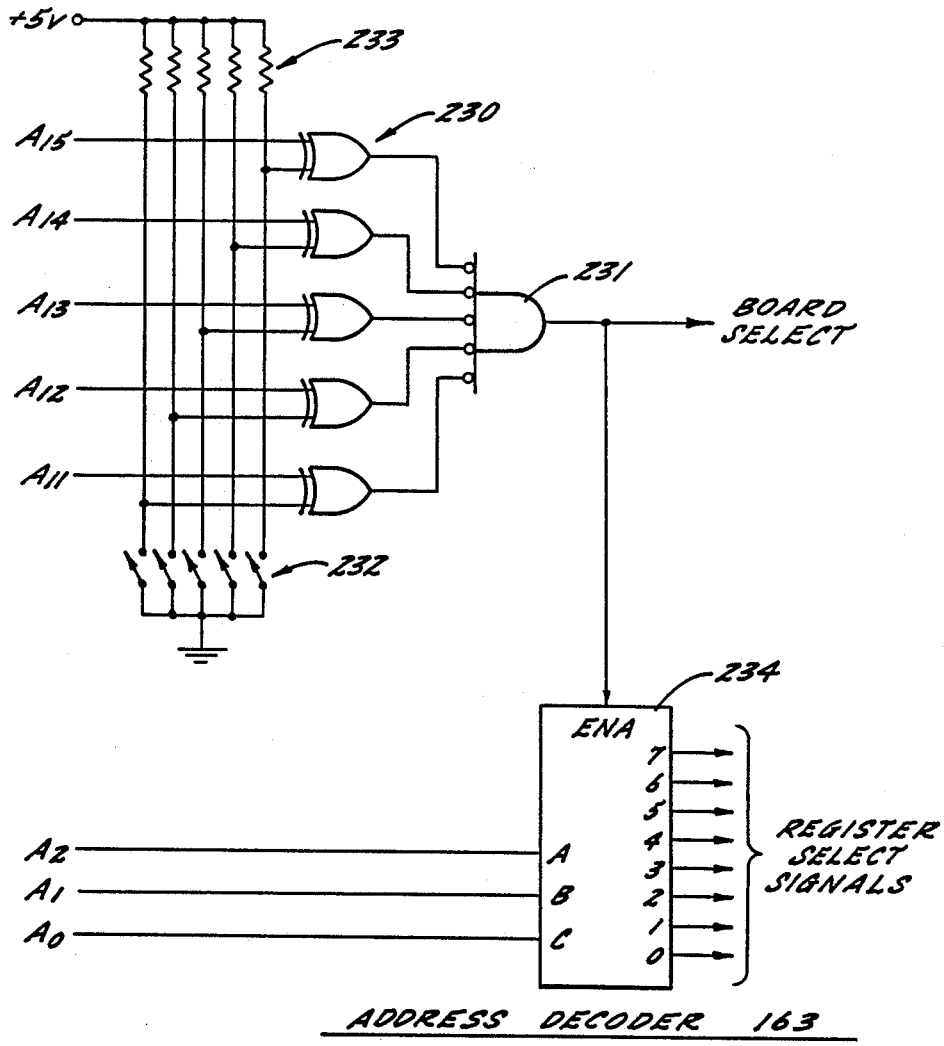
FIG. 20 is a detailed schematic diagram of an address decoder.

Turning now to FIG. 20, there is shown a schematic diagram of the address decoder 163. The highest order addresses ($A_{15}$–$A_{11}$) are fed to respective exclusive OR gates generally designated 230. These gates are, for example, part no. 74LS86. The outputs of the exclusive OR gates are combined by a NOR gate 231 such as part no. 74LS260. The NOR gate 231, therefore, generates an active BOARD SELECT signal when the set of high order addresses ($A_{15}$–$A_{11}$) match programmed signals on the other inputs of the exclusive OR gates 230. These programmed inputs are selected by a set of switches generally designated 232 and pull-up resistors generally designated 233 The pull-up resistors 233 are, for example, 1K ohm resistors.

In order to provide register select signals, the BOARD SELECT signal enables a 3 to 8 line decoder 234 which decodes the three least significant address bits ($A_2$, $A_1$, $A_0$) The decoder 234 is, for example, part no. 74LS138, which provides register select signals which are active low.

Turning now to FIG. 21, there is shown a state diagram for an angle encoder of the kind providing quadrature outputs. Since the quadrature outputs are binary, they define four distinct states. By the definition of "quadrature", any transition in which both of the outputs change is illegal. Therefore, in the state diagram of FIG. 21, only the legal transitions are shown. When the shaft of the angle encoder is turned clockwise, for example, the states change in the clockwise direction, and conversely when the shaft is turned counterclockwise, the states change in the counterclockwise direction.

In order to provide an indication of angular position, it is necessary to increment or decrement a counter in response to a change in the state of the angle encoder. This can be done using either synchronous circuits or asynchronous circuits. A synchronous circuit is shown in FIG. 22. In order to obtain synchronous quadrature signals, the quadrature signals from the angle encoder are sampled by delay flip-flops or register 251. The delay flip-flops are, for example, part no. 74LS74. The flip-flops indicate the "next state" of the angle encoder. To indicate the "present state" of the angle encoder, there is provided a second pair of delay flip-flops 252. As indicated in the state diagram of FIG. 1, it is desired to count up or increment the counter only when the present state is (0,0) and the next state is (0,1). This change in state is detected by a four input AND gate 253. Similarly, the counter should counter down when the present state is (0,1) and the next state is (0,0). This condition is detected by a second four-input AND gate 254. It is convenient to use 4-bit synchronous counters having a count enable and a count up and count down control signal. For this purpose the outputs of the AND gates 253 and 254 are combined in a NOR gate 255 to provide a count enable signal asserted low. The up-/down control signal is provided by a $Q_1$ complement signal from the flip-flop 252. In this case the gates 253, 254 and 255 are provided in a single integrated circuit part no. 74LS55, and the angle counter is provided by two 4-bit synchronous up/down counters 256 and 257, such as part no. 74LS168.

The synchronous circuit of FIG. 22 has the advantage that a correct position value will always be indicated to the microcomputer, regardless of when the angle encoder changes its state. Therefore, the synchronous circuit of FIG. 22 is useful for relatively inexpensive angle encoders which do not have circuits such as Schmitt triggers which would permit the quadrature signals to directly clock the counter. Such Schmitt triggers are, however, sometimes provided and the logic circuitry can be somewhat simplified in this case. Also, if Schmitt triggers are used, the quadrature signals can be used to interrupt the microcomputer when the angle changes its state. By using the interrupt technique, the programming for the microcomputer can be somewhat simplified. If a synchronous circuit is used, the microcomputer must monitor the angle counter and detect when the angle becomes incremented or decremented by more than one count. In other words, the microcomputer must be programmed to perform the Schmitt trigger function. On the other hand, if the asynchronous circuit is used, then the microcomputer can be interrupted when a change in angle occurs, and an interrupt routine can then strobe the analog-to-digital converters in the interface circuit (50 in FIG. 18) to obtain a set of numerical values coincident with the change in angle. Therefore, the synchronous and asynchronous circuits each have certain advantages and disadvantages, and the preferred circuit depends upon whether the angle encoder is provided with the Schmitt trigger circuits.

As shown in FIG. 23, the asynchronous circuit includes a single delay flip-flop 261 which detects whether the quadrature output $\phi_1$ leads or lags the quadrature output $\phi_2$. The quadrature outputs are combined in a NAND gate 262 to provide a clocking signal asserted low. This clocking signal is gated by the outputs of the flip-flop 261 in respective NAND gates 263 and 264 to determine respective clocking signals for counting up and counting down. In this case a pair of dual clock 4-bit counters 265 and 266 provide an angle counter. These counters are, for example, part no. 74LS193, and they have separate respective clock inputs for counting up and counting down.

In order to generate an interrupt signal whenever a count up or count down occurs, the outputs of the NAND gates are combined in another NAND gate 267; the four NAND gates 262, 263, 264 and 267 are included in a single integrated circuit, part no. 74LS00. The output of the gate 267 clocks a delay flip-flop 268 which is wired as a toggle flip-flop to divide the frequency of the clocking signal by two. A pair of switches 269 and 270 are provided to select an interrupt for either every cycle of the angle encoder or every two cycles. The selected clocking signal sets a set-reset flip-flop comprised of a pair of NAND gates 271 and 272. This set-reset flip-flop is reset by the BOARD SELECT signal from the address decoder (163 in FIGS. 18 and 20). Therefore, the set-reset flip-flop functions as a "handshake" flip-flop which acknowledges processing by the interrupt routine.

Figure 24:
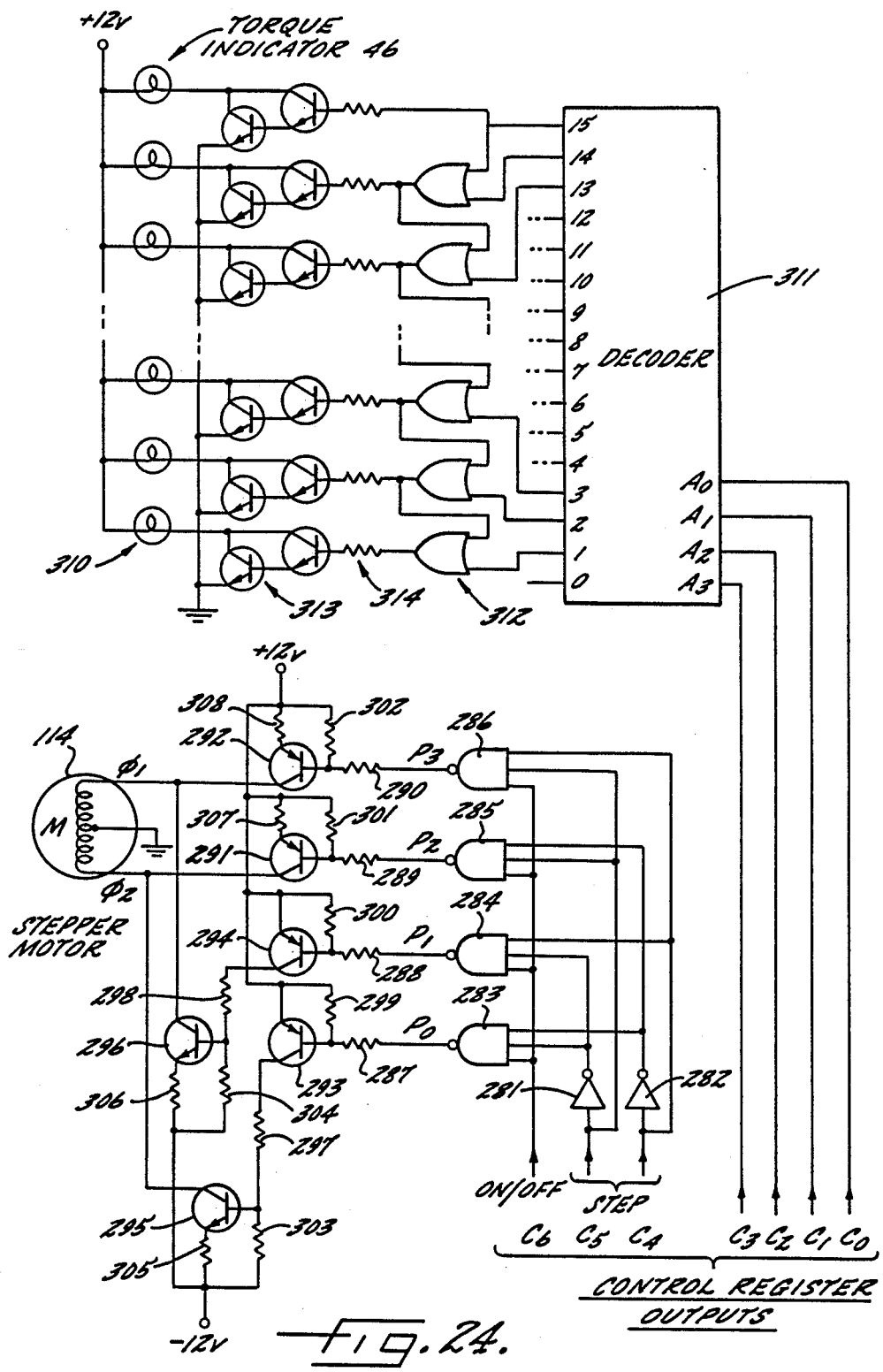
FIG. 24 is a detailed schematic diagram of circuits for activating a stepper motor to adjust the resistance in the hydraulic circuit of FIG. 14 and for indicating torque.

Turning now to FIG. 24, there are shown circuits for permitting the microcomputer to drive the stepper motor 114 to adjust the resistance of the hydraulic circuit, and to drive the torque indicator 46.

In order to step the stepper motor, the output bit $C_6$ is used to pulse the windings of the stepper motor, and the output bits $C_5$ and $C_4$ are decoded to indicate a particular one of four phases driving the stepper motor. The decoding of the four phases provided by a pair of inverters 281, 282 and four triple input NAND gates 283, 284, 285 and 286. To provide isolation between the logic power supply and the power supply for the stepper motor 114, the NAND gates 283, 286 preferably have open-collector outputs. They are for example, part no. 74LS12. Therefore, when the control bit $C_6$ is active, a selected one of the NAND gates is active low and its open-collector output sinks current from the positive supply voltage to the stepper motor. This current is limited by a respective one of four resistors 287, 288, 289 and 290. These resistors have values, for example, of 470 ohms. The current sinked by the NAND gates 285 and 286 turn on respective stepper motor driver transistors 291 and 292. Respective currents sinked by the NAND gates 283 and 284 turn on respective transistors 293 and 294 which reflect current to respective stepper motor driver transistors 295 and 296. The reflected current is limited by respective resistors 297 and 298, which are, for example, of 470 ohm resistors. The stepper motor driver circuit also includes resistors 299–304 which shunt leakage currents and have values, for example, of 1K oh. In order to limit the current drive to the stepper motor and to protect the driver transistors in the event of a short circuit or during transient conditions, the emitters of the driver transistors are connected to current limiting resistors 305, 306, 307 and 308. These resistors have values, for example, of 10 ohms.

In order to indicate torque, the torque indicator 46 includes a set of lamps generally designated 310 which display a bar graph. The control register output bits $C_3$ to $C_0$ specify a particular one of fifteen possible maximum values for the bar graph display. This maximum level is detected by a 4 to 16 decoder, such as part no. 4067. A respective one of the indicator lamps 310 is illuminated in response to the maximum level. In addition, all of the other indicator lamps below it in the bar graph should be illuminated as well. For this purpose, there is provided a string of OR gates 312 such as part no. 4019. Respective Darlington transistor pairs generally designated 313 are selectively turned on by the logic signals from the OR gates 312 and provide a sufficiently high current sinking capability to turn on the lamps. Respective resistors 314 limit the amount of current which the Darlington transistor pairs 313 sink from the gates 312. The resistors 314, for example, have values of 10K ohms. It should be noted that the microcomputer (51 in FIG. 1) is free to assign the particular values of torque which are indicated by the torque indicator 46. Therefore, the levels indicated by the bar graph need not be linearly spaced and, for psychological reasons, the mid-level can always be used to indicate the desired level of torque for the examination of a particular patient.

In view of the above, there has been provided noninvasive instrumentation and methodology for use by the practicing physician for the routine diagnosis of arthritis. The articulated leg restraint subjects the knee to control conditions which more accurately simulate the loading conditions experienced by the patient during daily life. Specifically, the articulated leg restraint permits acoustic signals to be recorded when the joint is moved at a predetermined angular velocity and against a predetermined resistance providing a constant torque. To provide the practicing physician with real-time data analysis and display, a microcomputer interface circuit preprocesses the acoustic signal to provide the microcomputer with the instantaneous frequency and amplitude of the acoustic signal occurring at predetermined values of joint angle, for example, at each degree of joint angle over a certain range during flexion or extension. The instantaneous frequency data provide an additional dimension for diagnosis of joint disease by pattern recognition techniques. The microcomputer may graph the instantaneous frequency and amplitude as a function of the joint angle during examination, and the practicing physician can visually recognize features of these graphs which tend to suggest the presence of joint disease. The data for a previous examination or for representative conditions of joint disease could be displayed simultaneously with the graph of newly obtained data to facilitate such a comparison and to indicate any change in the patient's condition. The data from an examination are easily stored on a magnetic disk for future reference.

It should be apparent that the system as described above can be modified in various ways. To reduce the cost of the system, for example, the torque indicator 46 and the stepper motor 114 along with their interface circuits shown in FIG. 24 could be offered as options.

Circuitry has been described for using either an optical shaft encoder or a potentiometer for measuring the angular position of the swinging arm. It should be noted, however, that any kind of position sensor could be used for measuring the angular position of the swinging arm. Suitable alternative positions sensors, for example, include inductive or magnetic sensors employing a synchro or Hall effect devices.

The torque has been described as being sensed by a pressure sensor. It should be readily apparent, however, that the torque could be sensed by a mechanical strain gage cell disposed on the crank shaft or the upper portion of the swinging arm.

What is claimed is:

1. A method of examining a patient for signs of disease or damage related to a joint defining an angle between at least two bones while permitting relative angular movement between said bones, said method including the steps of:
    (a) sensing acoustic signals emitted from said joint during said relative angular movement of said bones over a certain range of said angle while applying a resistance to said relative angular movement of said bones, and
    (b) obtaining an indication of the presence of disease or damage related to said joint from the sensed acoustic signals.

2. The method as claimed in claim 1, wherein the torque applied to said joint by virtue of said resistance is sensed during said step of sensing acoustic signals.

3. The method as claimed in claim 2, wherein an indication of the sensed torque is displayed to said patient during said step of sensing acoustic signals, whereby said patient may exert a selected amount of muscular force sufficient to keep the indicated torque substantially constant during said step of sensing acoustic signals.

4. The method as claimed in claim 1, wherein said resistance increases sharply when the relative angular velocity of said bones exceeds a predetermined value, whereby said sensing of acoustic signals occurs during relative motion of said bones at a substantially constant velocity.

5. The method as claimed in claim 1, wherein said acoustic signals are sensed by an accelerometer mounted to said joint.

6. A method of examining a patient for signs of disease or damage related to a joint defining an angle between at least two bones while permitting relative angular movement between said bones, said method including the steps of:
    (a) sensing acoustic signals emitted from said joint during relative angular movement of said bones over a certain range of said angle,
    (b) determining the amplitudes of said acoustic signals,
    (c) determining the instantaneous frequencies of said acoustic signals, and
    (d) determining values of said angle during said movement, and
    (e) associating both the determined amplitudes and instantaneous frequency with said values of said angle to obtain an indication of the presence of disease or damage related to said joint.

7. The method as claimed in claim 6, further comprising the steps of displaying graphs of said amplitudes and instantaneous frequencies as a function of said angles of said joint.

8. The method as claimed in claim 6, further comprising the steps of arranging said amplitudes and instantaneous frequencies in arrays of data values which specify the amplitudes and instantaneous frequencies of said acoustic signals occurring for predetermined joint angles within said angular range.

9. The method as claimed in claim 6, wherein said step of determining values of said angle includes sensing the angle of an articulated restraint having respective members which track the relative motion of respective ones of said bones.

10. The method as claimed in claim 6, wherein a resistance to said relative angular movement of said bones is applied during said step of sensing acoustic signals 11. The method as claimed in claim 10, wherein the torque applied to said joint by virtue of said resistance is sensed during said step of sensing acoustic signals.

12. The method as claimed in claim 11, wherein an indication of the measured torque is displayed to said patient during said steps of sensing acoustic signals, whereby said patient may exert a selected amount of muscular force sufficient to keep the indicated torque substantially constant during said step of sensing acoustic signals.

13. The method as claimed in claim 10, wherein said resistance increases sharply when the relative angular velocity of said bones exceeds a predefined value, whereby said sensing of acoustic signals occurs during relative motion of said bones at a substantially constant velocity.

14. The method as claimed in claim 6, wherein said acoustic signals are sensed by an accelerometer.

15. An apparatus for examining a patient for signs of disease or damage related to a joint defining an angle between at least two bones while permitting relative angular movement between said bones, said apparatus comprising, in combination,
  means for sensing acoustic signals emitted from said joint during said relative angular movement of said bones over a certain range of said angle;
  means for determining the amplitudes of said acoustic signals;
  means for determining the instantaneous frequencies of said acoustic signals;
  means for sensing values of said angle which occur during said relative angular movement of said bones; and
  means for associating the amplitudes and the instantaneous frequencies with the sensed values of said angle such that the amplitude and instantaneous frequency of an acoustic signal is associated with the values of the angle at which the acoustic signal is emitted, whereby there is obtained an indication of the presence of disease or damage related to said joint.

16. The apparatus as claimed in claim 15, further comprising means for displaying graphs of said amplitudes and instantaneous frequencies as a function of the value of said angle.

17. The apparatus as claimed in claim 15, further comprising memory means for storing said amplitudes and instantaneous frequencies as arrays of data values which specify the amplitudes and instantaneous frequencies of said acoustic signals occurring for predetermined joint angles within said angular range.

18. The apparatus as claimed in claim 15, further comprising means for applying a resistance to said relative angular movement of said bones.

19. The apparatus as claimed in claim 18, further comprising means for sensing the torque applied to said joint by virtue of said resistance during said relative angular movement of said bones.

20. The apparatus as claimed in claim 18, wherein said resistance is a sharply increasing function of the relative angular velocity of said bones above a predefined value.

* * * * *